(12) United States Patent
Chen et al.

(10) Patent No.: US 6,979,543 B2
(45) Date of Patent: *Dec. 27, 2005

(54) METHOD FOR DETECTING BIOLOGICAL AGENTS

(75) Inventors: Liaohai Chen, Los Alamos, NM (US); Duncan W. McBranch, Santa Fe, NM (US); Hsing-Lin Wang, Los Alamos, NM (US); David G. Whitten, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/412,568

(22) Filed: Apr. 10, 2003

(65) Prior Publication Data

US 2004/0023272 A1 Feb. 5, 2004

Related U.S. Application Data

(62) Division of application No. 09/565,589, filed on May 4, 2000, now Pat. No. 6,589,731.

(60) Provisional application No. 60/132,556, filed on May 5, 1999.

(51) Int. Cl.$^7$ ............................................. C12Q 1/68
(52) U.S. Cl. ..................... 435/6; 422/68.1; 422/82.01; 422/82.02; 422/82.05; 422/82.08; 435/4; 435/5; 435/174; 435/175; 435/176; 435/177; 435/180; 435/287.1; 435/287.2; 435/808; 435/966; 436/164; 436/172; 436/504; 436/512; 436/518; 436/524; 436/528; 436/529; 436/805; 436/806; 436/808; 436/823; 530/300; 530/350; 530/387.1; 530/388.1; 530/391.1; 530/811; 530/812; 536/23.1; 536/24.3; 536/24.31; 536/24.32; 536/25.32

(58) Field of Search ................................ 435/4, 5, 6, 7, 435/91.1, 91.2, 94, 174–177, 180, 181, 183, 435/270, 287.1, 287.2, 808, 966; 436/164, 436/172, 501, 504, 518, 524, 528, 529, 805, 436/806, 808, 823, 512; 422/68.1, 82.01, 422/2, 82.05, 82.08; 530/300, 350, 387.1, 530/388.1, 388.2, 391.1, 811, 812, 815; 536/23.1, 536/24.3, 24.31, 24.32, 25.32

(56) References Cited

U.S. PATENT DOCUMENTS 4,724,202 A * 2/1988 Dattagupta et al. ............ 435/6
5,280,548 A * 1/1994 Atwater et al. ............... 385/12

(Continued)

OTHER PUBLICATIONS

Zhou et al. Fluorescent Based on Energy Migration in Conjugated Polymers: The Molecular Wire Approach to Increased Sensitivity. J.Am. Chem. Soc. vol. 117, pp. 12593-12602 (1995).*

Primary Examiner—Christopher L. Chin
(74) Attorney, Agent, or Firm—DLA Piper Rudnick Gray Cary US LLP

(57) ABSTRACT

A sensor is provided including a polymer capable of having an alterable measurable property from the group of luminescence and electrical conductivity, the polymer having an intermediate combination of a recognition element, a tethering element and a property-altering element bound thereto and capable of altering the measurable property, the intermediate combination adapted for subsequent separation from the polymer upon exposure to an agent having an affinity for binding to the recognition element whereupon the separation of the intermediate combination from the polymer results in a detectable change in the alterable measurable property, and, detecting said detectable change in the alterable measurable property.

13 Claims, 9 Drawing Sheets

Highly Fluorescent

Nonfluorescent

Nonfluorescent

Highly Fluorescent

U.S. PATENT DOCUMENTS

| | | | |
|---|---|---|---|
| 5,364,797 A * | 11/1994 | Olson et al. | 436/501 |
| 5,466,575 A * | 11/1995 | Cozzette et al. | 435/6 |
| 5,656,739 A * | 8/1997 | Cubicciotti | 536/23.1 |
| 5,739,305 A * | 4/1998 | Cubicciotti | 536/23.1 |
| 5,759,767 A * | 6/1998 | Lakowicz et al. | 435/4 |
| 5,981,695 A * | 11/1999 | Mattes et al. | 528/492 |
| 6,743,640 B2 * | 6/2004 | Whitten et al. | 436/518 |
| 2002/0150759 A1 * | 10/2002 | Jones et al. | 428/403 |

\* cited by examiner

Biotin/Methyl Viologen

Tailored ligand/tether/quencher

METHOD FOR DETECTING BIOLOGICAL AGENTS

This application is a divisional application of U.S. patent application Ser. No. 09/565,589 filed May 4, 2000, now U.S. Pat. No. 6,589,731 B1, incorporated herein by reference U.S. patent application Ser. No. 09/565,589 claims benefit of U.S. patent application Ser. No. 60/132,556, filed May 5, 1999. The entirety of U.S. patent application Ser. No. 60/132,556 is also incorporated herein by reference.

FIELD OF THE INVENTION

The present invention relates to highly sensitive biological and chemical sensors, to a method for the detection of biological and chemical agents using such sensors and to a chemical moiety combination used in such sensors and in such detection methods. This invention is the result of a contract with the Department of Energy (Contract No. W-7405-ENG-36).

BACKGROUND OF THE INVENTION

Biosensors are sensors that detect chemical species with high selectivity on the basis of molecular recognition rather than the physical properties of analytes. See, e.g., Advances in Biosensors, A. P. F. Turner, Ed. JAI Press, London, (1991). Many types of biosensing devices have been developed in recent years, including enzyme electrodes, optical immunosensors, ligand-receptor amperometers, and evanescent-wave probes.

The detection mechanism in such sensors can involve changes in properties such as conductivity, absorbance, luminescence, fluorescence and the like. Various sensors have relied upon a binding event directly between a target agent and a signaling agent to essentially turn off a property such as fluorescence and the like. The difficulties with present sensors often include the size of the signal event which can make actual detection of the signal difficult or affect the selectivity or make the sensor subject to false positive readings.

Amplification of fluorescence quenching has been reported in conjugated polymers. For example, Swager, Accounts Chem. Res., 1998, v. 31, pp. 201–207, describes an amplified quenching in a conjugated polymer compared to a small molecule repeat unit by methylviologen of 65; Zheng et al., J. Appl. Polymer Sci., 1998, v. 70, pp. 599–603, describe a Stern-Volmer quenching constant of about 1000 for poly(2-methoxy,5-(2' -ethylhexloxy)-p-phenylene-vinylene (MEH-PPV) by fullerenes; and, Russell et al., J. Am. Chem. Soc., 1982, v. 103, pp. 3219–3220, describe a Stern-Volmer quenching constant for a small molecule (stilbene) in micelles of about 2000 by methylviologen. Despite these successes, continued improvements in amplification of fluorescence quenching have been sought. Surprisingly, a $K_{sv}$ of greater than $10^5$ has now been achieved.

It is an object of the present invention to provide a specific sensing system wherein the sensor can yield a distinctly recognizable signal event upon the binding of a target agent by a recognition element of the sensor.

It is a further object of the invention to provide a chemical moiety for use in a sensor system, the chemical moiety including a recognition element, a tethering element and a property-altering element.

SUMMARY OF THE INVENTION

To achieve the foregoing and other objects, and in accordance with the purposes of the present invention, as embodied and broadly described herein, the present invention provides a sensor including a polymer capable of having an alterable measurable property from the group of luminescence and electrical conductivity, the polymer having an intermediate combination of a recognition element, a tethering element and a property-altering element bound thereto so as to alter the measurable property, the intermediate combination adapted for subsequent separation from the polymer upon exposure to an agent having an affinity for binding to the recognition element whereupon the separation of the intermediate combination from the polymer results in a detectable change in the alterable measurable property, and, a means of detecting said detectable change in the alterable measurable property.

The present invention further provides a method of detecting a biological agent including contacting a sample with a sensor including a polymer capable of having an alterable measurable property from the group of luminescence and electrical conductivity, the polymer having an intermediate combination of a recognition element, a tethering element and a property-altering element bound thereto so as to alter the measurable property, the intermediate combination adapted for separation from the polymer upon exposure to a biological agent having an affinity for binding to the recognition element whereupon the separation of the intermediate combination from the polymer results in a detectable change in the alterable measurable property; and, detecting said detectable change in the alterable measurable property.

The present invention still further provides a chemical moiety including a recognition element, tethering element and property-altering element bound together in combination wherein the recognition element is bound to the tethering element and the tethering element is bound to the property-altering element, the combination adapted for complexation with a polymer having an alterable measurable property selected from the group of luminescence and electrical conductivity.

The present invention still further provides a kit for the detection of biological agents, the kit including a fluorescent polymer and a chemical moiety including a recognition element, which binds to a target biological agent, and a property-altering element which fluoresces or changes fluorescence to a distinguishable degree bound together by a tethering element, said chemical moiety adapted for complexation with a fluorescent polymer, wherein, in the presence of binding of said recognition element to said target biological agent, the fluorescence emitted by said polymer is altered from that emitted when said binding between said recognition element and said target biological agent does not occur.

BRIEF DESCRIPTION OF THE DRAWINGS

FIG. 8 shows the chemical structure of GM1-MV, a combination chemical moiety, of the present invention.

DETAILED DESCRIPTION

The present invention is concerned with a system for effective sensing of biological agents by observing fluorescence changes or electrical conductivity changes. In one embodiment, the system includes a highly fluorescent molecule and a fluorescence quencher molecule bound though a tether molecule to a receptor element.

Figure 1A:
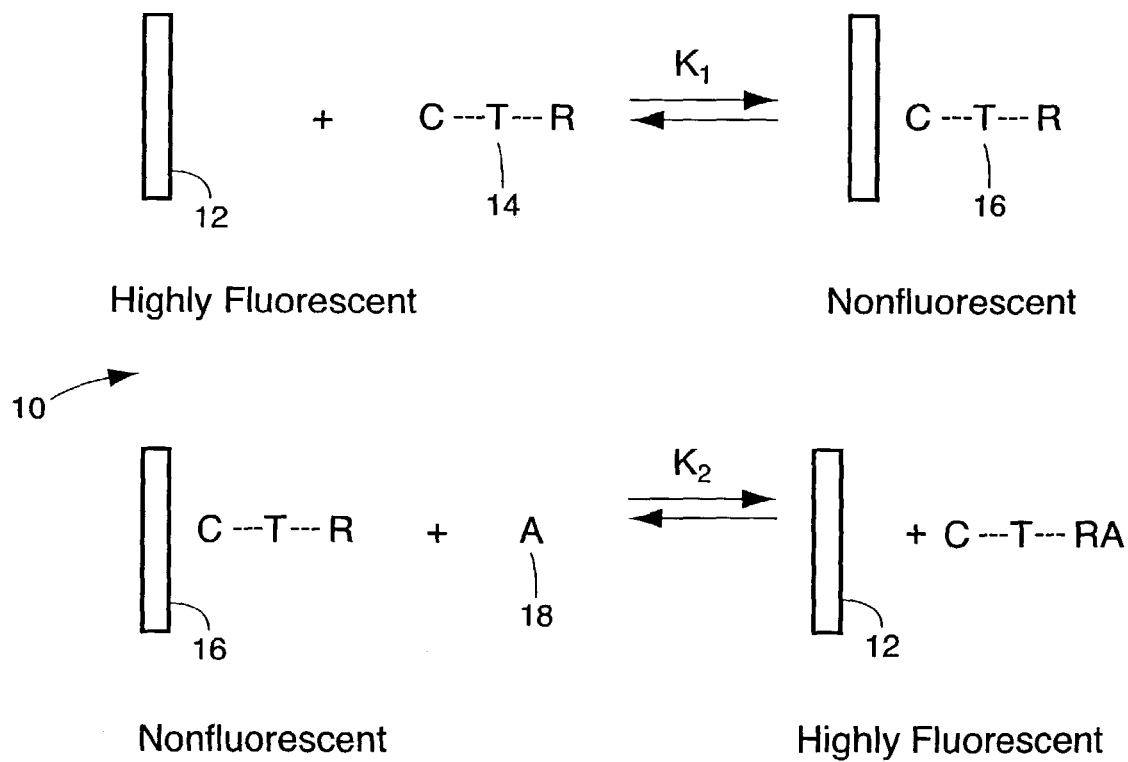
FIG. 1(a) shows a schematic representation of a system of the present invention and FIG. 1(b) shows the chemical structure of B-MV, a combination chemical moiety, of the present invention.
Figure 1B:
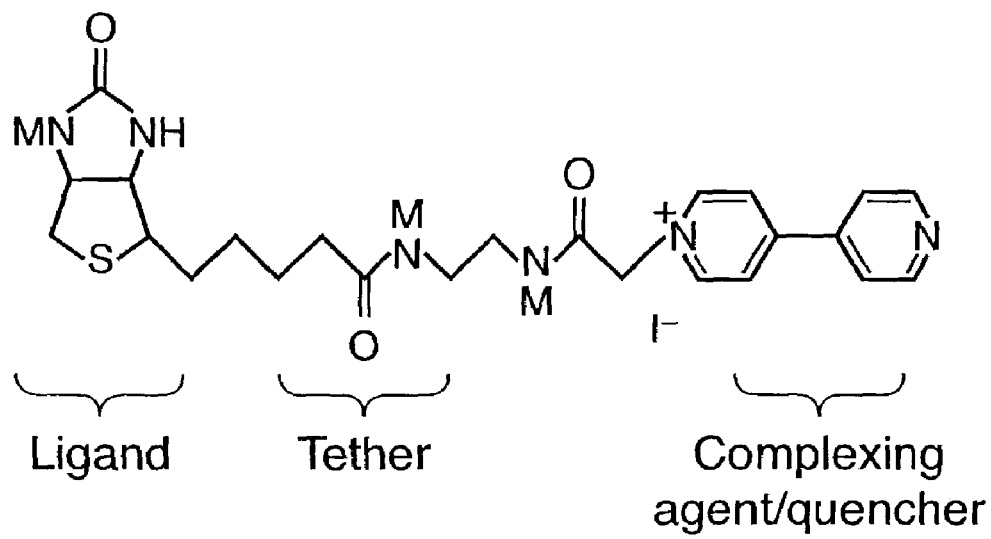
Figure 2:
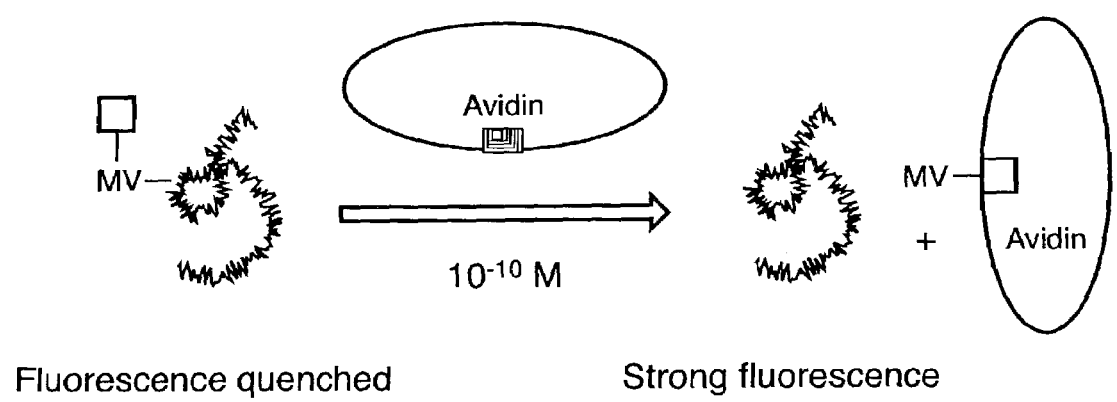
FIG. 2 shows a diagram of a biosensing embodiment of the present invention wherein a strong fluorescence signal is obtained upon separation of a bound biological recognition element, tethering element and property-altering element (fluorescence quencher) combination from a polymer through the greater affinity of a biological agent for the biological recognition element.
Figure 3:
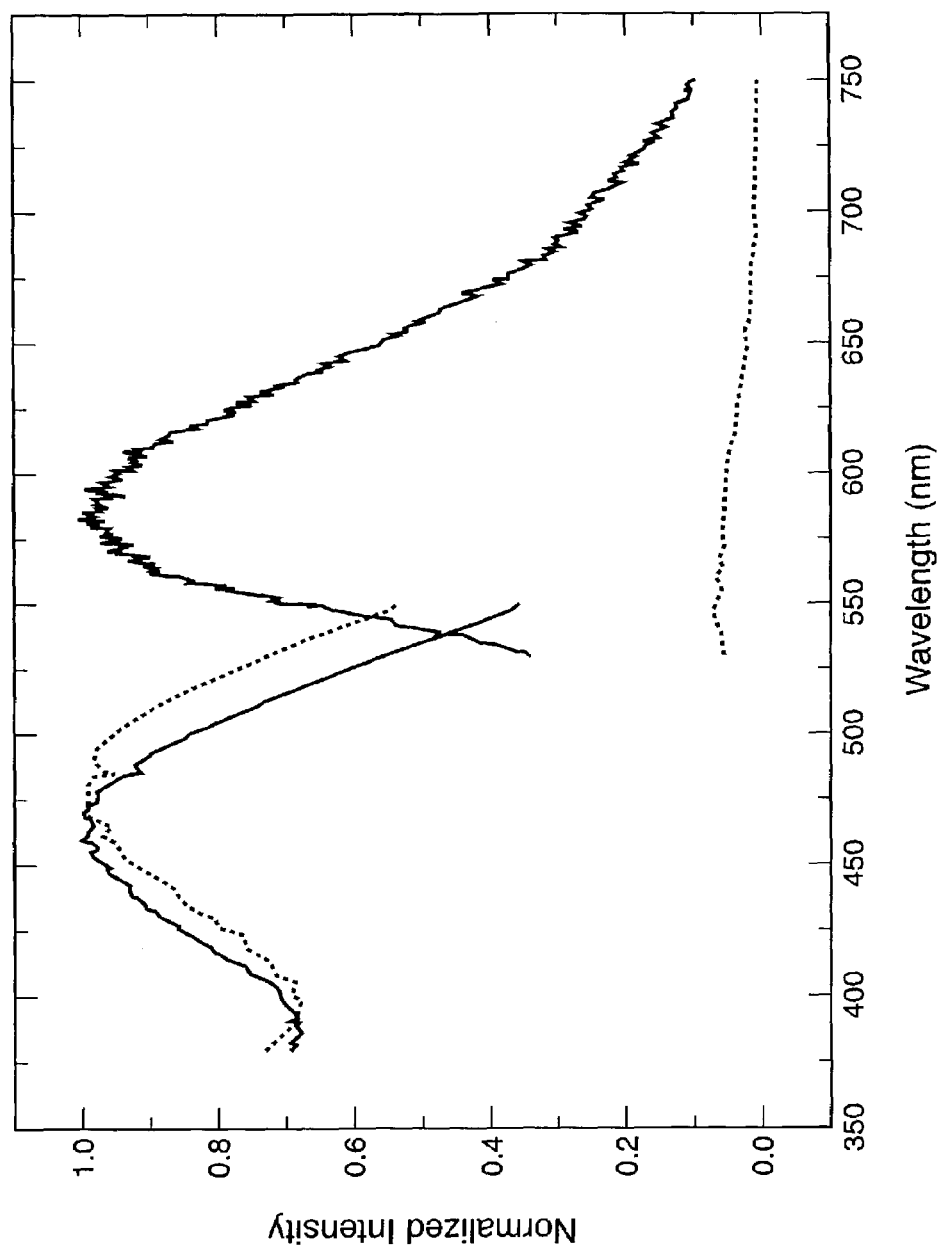
FIG. 3 shows a graph of the absorption and fluorescence spectra of an embodiment of the polymer and the polymer with a bound fluorescence quencher in accordance with the present invention.
Figure 4:
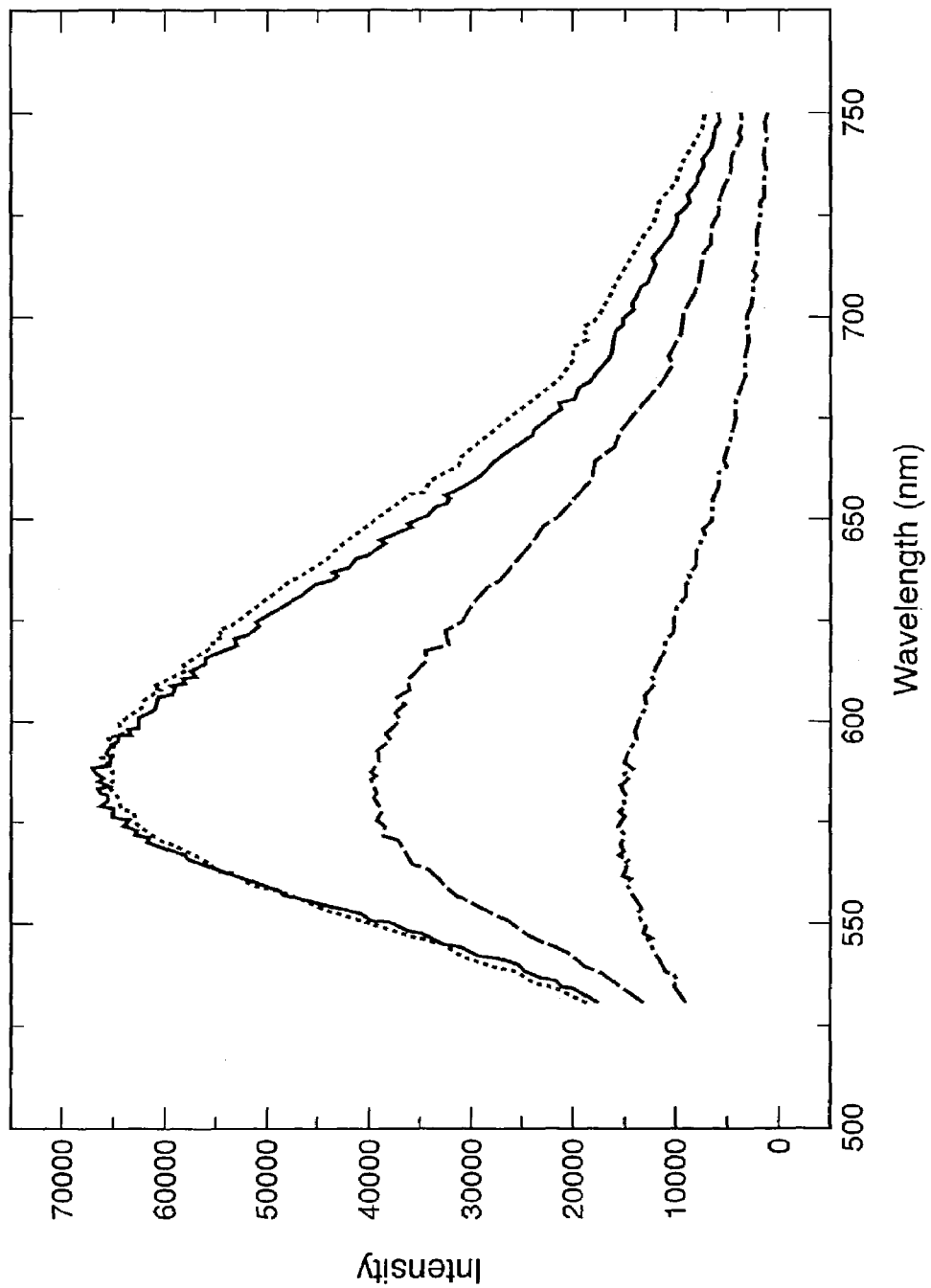
FIG. 4 shows a graph of the fluorescence spectra of an embodiment of the polymer and the polymer with a bound biological recognition element and fluorescence quencher combination both initially and following the addition of various levels of a biological agent in accordance with the present invention.
Figure 5:
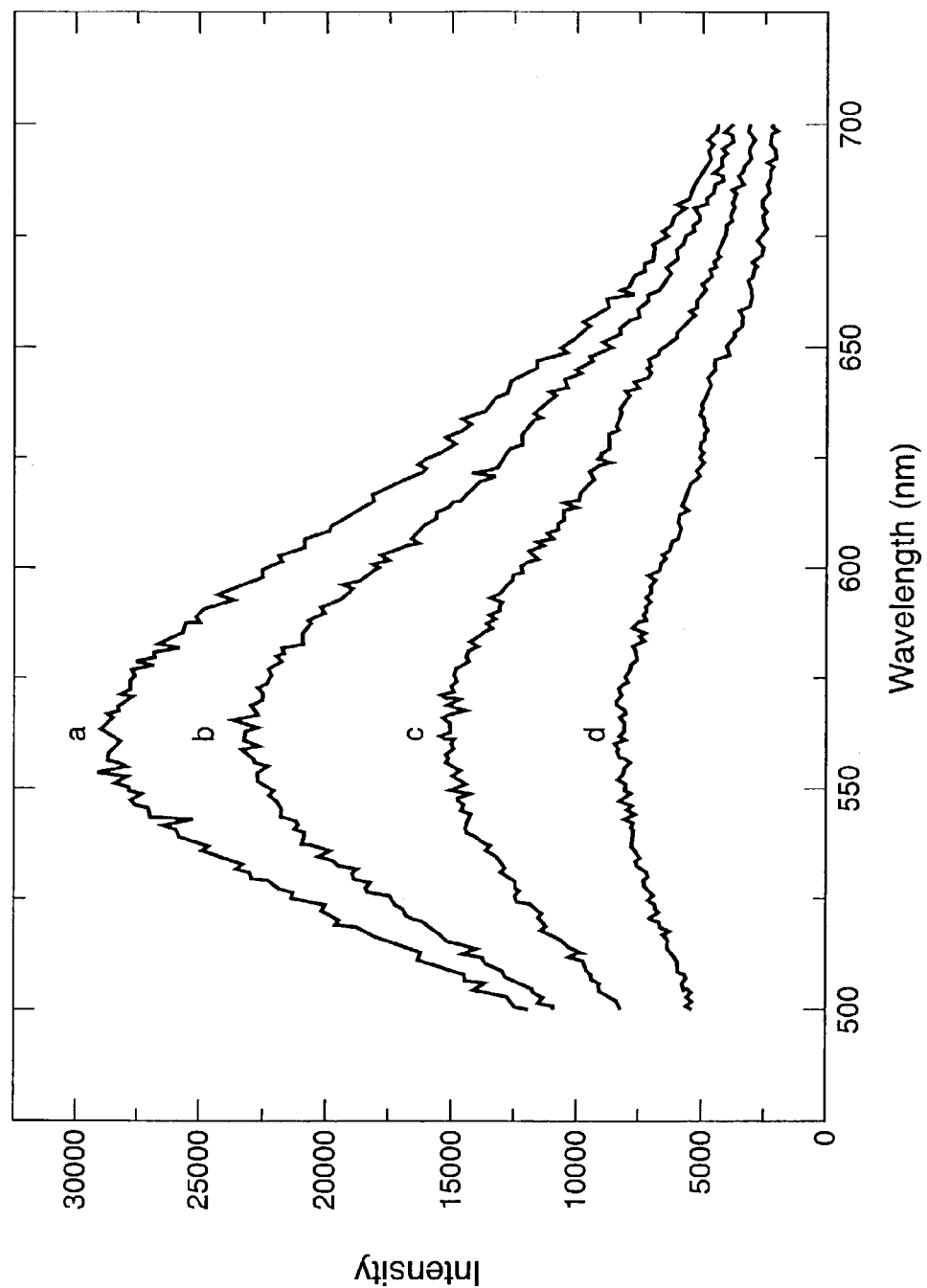
FIG. 5 shows a graph illustrating the fluorescence of a solid film of a polymer in accordance with the present invention both initially and following the exposure to a chemical agent.

In FIG. 1(a), a schematic representation of the present invention is shown. The sensor system 10 of the present invention includes a highly fluorescent molecule 12, preferably a polymer, shown together with a property-altering element (C) bound through a tethering element (T) to a recognition element (R) combination 14. When combination 14 is bound to molecule 12, a nonfluorescent combination 16 is formed. As shown in FIG. 1(b), when the sensor system 10 is contacted by a biological agent 18, and the property-altering element (C) bound through the tethering element (T) to the recognition element (R) combination 14 is more highly attracted to the biological agent 18 than to highly fluorescent molecule 12 (i.e., $K_2>>K_1$), the nonfluorescent combination 16 is broken to yield the highly fluorescent molecule 12 and such a fluorescent signal event can be detected to indicate the presence of the biological agent 18.

The key to the system in one embodiment of the present invention is that in the absence of the agent to be detected, complexing (binding or association) of the polymer with the intermediate combination (C-T-R) results in little or no fluorescence. C refers to a complexing agent also referred to as a property-altering element. T refers to a tethering agent or element. R refers to a recognition element and is sometimes referred to as a receptor or recognition ligand for recognizing and binding to a target agent such as a target chemical or biological agent, usually a biological agent. However, when the biological agent is present, the much stronger binding constant or association of the recognition element with the biological agent, combined with the desired requirement that the biological agent—recognition element complex is sterically too bulky to allow the property-altering element to be complexed with or by the polymer, leads to the release or separation of the intermediate combination (C-T-R) from the polymer and to an easily detectable signal event such as renewed fluorescence. The present system can have particularly high sensitivity since it results in a fluorescence increase upon "recognition" of the biological agent against a background of little or no fluorescence at the detection wavelength. One example of such a C-T-R combination is shown in FIG. 1(*b*).

In the sensor of the present invention, the recognition event, signal transduction and amplification coincide. In the absence of the biological agent, in one embodiment the sensor of the present invention would remain in an essentially undetectable stage, i.e., remain off, due to little or no fluorescence at the detection wavelength. It is expected that one embodiment of a sensor in accordance with the present invention can have little or no background interference. It is further expected that since the excited state on the polymer can be quenched, the lifetime should be very short and little or no photobleaching of the polymer (as a fluorescent molecule) should occur.

The polymer used in the present invention can be a luminescent molecule such as a fluorescent molecule or can be a conductive molecule. Suitable luminescent polymers can include luminescent conjugated materials such as, e.g., a poly(phenylene vinylene) such as poly(p-phenylene vinylene) (PPV), polythiophene, polyphenylene, polydiacetylene, polyacetylene, poly(p-naphthalene vinylene), poly(2,5-pyridyl vinylene) and derivatives thereof such as poly(2,5-methoxy propyloxysulfonate phenylene vinylene) (MPS-PPV), poly(2,5-methoxy butyloxysulfonate phenylene vinylene) (MBS-PPV) and the like. For water solubility, derivatives can include one or more pendent ionic groups such as sulfonate and methyl ammonium. For example, pendent groups could include $-O-(CH_2)_n-OSO_3^-(M^+)$, where a preferred form would have n=3 or 4 and $M^+=Na^+$ or $Li^+$, $-(CH_2)_n-OSO_3^-(M^+)$, where a preferred form would have n=3 or 4 and $M^+=Na^+$ or $Li^+$, $-O-CH_2)_n-N^+(CH_3)_3\ (X^-)$, where a preferred form would have n=3 or 4 and $X^-=Cl^-$ and $-(CH_2)_n-N^+(CH_3)_3\ (X^-)$, where a preferred form would have n=3 or 4 and $X^-=Cl^-$. Water-polyelectrolytes such as MPS-PPV and MBS-PPV and the like are especially preferred in some embodiments. Suitable conductive polymers can include polyaniline, polypyrrole, polyfuran, polyvinyl carbazole and derivatives thereof. Such a polymer can be: in the form of a film on a variety of substrate surfaces, e.g., on a fiber optic probe, on tethered sols or beads or on micro-latex particles, or on a soluble substrate, i.e., in a suitable liquid medium, and the like. The polymer can be in the form of a gel, a porous support or a membrane.

The sensors of the present invention may be used to detect either biological agents or chemical agents. However, it is expected that such sensors may have greater advantages in the detection of selected biological agents wherein there is a matching pair of a biological recognition element and a biological agent having a high affinity (a high K) that trigger the binding and subsequent signal event. For example, the detected biological agent can be from among the group of proteins, amino acids, oligonucleotides, hormones, vitamins, viruses, bacteria, cells, microorganisms, antibody fragments, and toxins. Exemplary of such agents are included the following: influenza, parainfluenza, hepatitis, *streptococcus, staphylococcus,* HIV, anthrax, cholera, and the like.

The polymer used in the sensor of the present invention is capable of having an alterable measurable property selected from the group of luminescence and electrical conductivity. For example, the polymer can be capable of producing a detectable fluorescence signal upon exposure to one or more selected wavelengths of light. Such a detectable fluorescence signal can be an increased signal, a decreased signal or can be shifted in wavelength. This change in fluorescence is then detectable. Likewise, the polymer can be capable of having a measurable level of electrical conductivity under selected conditions.

The present invention involves an intermediate combination of a recognition element, a tethering element and a property-altering element. This intermediate combination is initially complexed with or bound to the polymer of the sensor so as to alter said alterable measurable property of the polymer. For example, the intermediate combination upon binding to or complexing with the polymer could alter the luminescence properties or electrical conductivity properties of the polymer to give an initial luminescence or electrical conductivity level. The intermediate combination is adapted for subsequent separation from the polymer upon exposure to an agent having an affinity for binding to the recognition element whereupon the separation of the intermediate combination from the polymer results in a detectable change in the alterable measurable property. That is, the release of the intermediate combination from the polymer at the time that the intermediate combination is taken up by the recognizable agent, whether a chemical or biological agent, would produce a detectable change in the alterable measurable property.

For example, the initial binding or complexation of the intermediate combination with the polymer could result in a fluorescence quenching or electrical conductivity quenching such that there is no fluorescence or electrical conductivity by the bound polymer. Upon exposure of the polymer including the bound intermediate combination to a recognizable agent whereupon the recognition element of the intermediate combination is bound to the particular agent and the intermediate combination is separated from the polymer, a fluorescent signal or electrical conductivity signal can be detected.

In a preferred embodiment of the present invention, the initial quenching of a signal can provide a low background or baseline property measurement such that a sensor can essentially be in the turned-off position. Then, upon the separation of the intermediate combination from the polymer, the sensor can be turned-on and an easily detectable event can occur.

The recognition element of the intermediate combination must be capable of recognizing and binding to a selected chemical or biological species, preferably a biological species. For example, the recognition element can be from among chemical ligands, antibodies, polynucleotides, antigens, polypeptides, and polysaccharides. Combinations of pairs that are categorizable as recognition element-chemical or biological species pairs are well know to those skilled in the art. For example, immunoassays are based on antigen-antibody affinity interactions. Similarly recognized pairs include: hormone-hormone receptor pairs; polynucleotide strand-complementary polynucleotide strand pairs; enzyme-enzyme cofactor or inhibitor pairs; avidin-biotin; protein A-immunoglobulin; and, lectins-specific carbohydrates.

Another recognized pair is cholera toxin (CT) and ganglioside GM1. Gangliosides are a class of molecules which are glycolipids. Different gangliosides have been identified as prominent cell surface constituents of various cells. Gangliosides are known as mono-, di-, tri or polysialogangliosides, depending upon the degree of glycosylation with sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the binding pattern observed for the molecule. Cholera toxin is an $AB_5$ hexameric protein with five identical B subunits which define the binding region and one A subunit responsible for catalysis. Toxicity of the cholera toxin is initiated by the recognition and binding of B sub-units to a pentasaccharide moiety of GM1 in the cell surface followed by a mechanism involved in the entry of an A sub-unit through the membrane into the cell.

A tethering element is of a length adapted to allow for the recognition element to extend to or reach the recognized site of a chemical or biological species. The tethering element can be tailored to the necessary length to allow the recognition element to reach a binding site on a chemical or biological species, preferably a biological species. This length can be as short as a single linking atom or may be up to as many as about 100 atoms in length, preferably from about 3 to about 25 atoms in length for the tethering element. Often, the recognition element and the species being recognized are specific (i.e., recognizing a single agent) or highly specific (i.e., recognizing a small group of agents) for one another. This specificity can be of a chemical nature, of a geometric nature or both. The recognition can be as specific as a "lock and key" arrangement where only a single recognition element will function to join with the recognized chemical or biological species.

The property-altering element can be, e.g., a fluorescent quencher or fluorescent enhancer, or a conductivity quencher or electrical conductivity enhancer. Similarly, the property-altering element need not completely quench a signal but could result only in a lessened signal that could be distinguishable from the signal resulting from a subsequent binding event. Also, the property-altering element could shift the spectra of a luminescence or fluorescence. Among suitable property-altering elements are included methyl viologen, squaraine, and other electron-accepting moieties.

The intermediate combination including the recognition element, the tethering element and the property-altering element combination is adapted for separation from the polymer. That is, upon the binding of the recognition element to the target species or agent, the affinity or binding constant between the recognition element and the target species must be high enough such that the property-altering element is separated from the polymer allowing for the detection of the change in alterable measurable property. Thus, when the intermediate combination has lead to a quenching of, e.g., a fluorescent signal, the removal of the intermediate combination from the polymer in the presence of the target species would allow the regeneration of the fluorescent event and allow the detection of the alterable measurable property. target species would allow the regeneration of the fluorescent event and allow the detection of the alterable measurable property.

Chemical agents recognizable by a chemical recognition element may include a large steric biomolecule for which a ligand exists or may be synthesized.

Various means of detecting the detectable change in the alterable measurable property are well known to those of skill in the art. For example, a spectrophotometer could measure the luminescence or fluorescence change. A voltage/current meter could measure the change in electrical conductivity of a polymer.

The present invention further includes a kit for the detection of biological agents. Such a kit can generally include a fluorescent polymer such as described previously and a chemical moiety as described previously.

The present invention is more particularly described in the following examples which are intended as illustrative only, since numerous modifications and variations will be apparent to those skilled in the art.

EXAMPLE 1

A substituted, water-soluble polyanionic derivative of PPV [poly(2,5-methoxy propyloxysulfonate phenylene vinylene), MPS-PPV] was studied together with its fluorescence properties and excited-state dynamics in the presence of a variety of organic and inorganic reagents whose behavior towards simple trans-stilbene derivatives has previously been investigated. The results have demonstrated the unique excited-state properties of conjugated polymers compared to single chromophore "molecular" excited states. In particular, the use of such a polymer has lead to a greater than million-fold amplification of the sensitivity to fluorescence quenching, relative to that of the single molecular chromophore in dilute solution. This amplification has been harnessed to demonstrate a versatile class of highly sensitive biological and chemical sensors, both in solution and in solid films.

MPS-PPV is a water-soluble polymer, with molecular weight estimated from light scattering measurements to be $1-5 \times 10^5$ (about 1000 monomer repeat units). The synthesis of MPS-PPV, poly(2,5-methoxy propyloxysulfonate phenylene vinylene), was as follows. The sodium salt of para-hydroquinone monomethyl ether was condensed with the lactone of 3-hydroxypropanesulfonic acid to yields the sodium salt of 1-methoxy-4-propyloxysulfonatobenzene. The salt was reacted with formaldehyde and hydrochloric acid in dioxane to yield the corresponding 2,5-di(chloromethyl) product. After purification, this product was reacted with t-butyl lithium in N,N-dimethylformamide at room temperature for 40 hours to yield the polymer.

The absorption and fluorescence spectra of MPS-PPV in diluted aqueous solution are similar to trans-stilbene and its derivatives, but shifted to longer wavelength due to the extended conjugation in the polymer. It is well established that excited states of trans-stilbene and related molecules are readily quenched by electron-deficient aromatic compounds in both dynamic and static processes. For example, the fluorescence of trans-stilbene derivatives can be quenched by N,N"-dimethyl-4,4"-bipyridinium (methyl viologen, $MV^{2+}$) by formation of relatively weak ground-state "donor-acceptor" complexes. While not wishing to be bound by the present explanation, the quenching can be described over specific concentration ranges by a conventional "Stern-Volmer" relationship:

$$\phi^\circ/\phi = 1 + K_{SV}[MV^{2+}]$$

where $\phi^\circ$ and $\phi$ are the quantum efficiencies (or intensities) of fluorescence in the absence and presence of $MV^{2+}$, respectively, and $[MV^{2+}]$ is the $MV^{2+}$ concentration. The constant $K_{SV}$, thus provides a direct measure of the quenching sensitivity. While the quenching of trans-stilbene by $MV^{2+}$ in homogeneous solution can only be observed at relatively high concentrations of $MV^{2+}$ ($K_{SV}=15$), it is much more easily detectable when trans-stilbene or its amphiphilic derivatives are incorporated into anionic assemblies such as micelles or bilayer vesicles. The amplification in quenching sensitivity from solution to anionic detergent (sodium lauryl sulfate) micelles ($K_{SV}=1\times10^3$) can be readily attributed to a "concentration enhancement" effect in which the stilbene and viologen are assembled by a combination of coulombic and entropic interactions in a microphase such that their "local" concentrations are greatly enhanced. Given the net negative charge on MPS-PPV, it was anticipated that it might readily bind $MV^{1+}$ in aqueous solution and lead to significant fluorescence quenching at moderate viologen concentrations. It was found that in dilute solutions of MPS-PPV ($10^{-5}$ M in monomer repeat units), addition of very low concentrations of $MV^{2+}$ leads to noticeable changes in the MPS-PPV absorption spectrum, and to a dramatic quenching of its fluorescence. The corresponding quenching constant ($K_{SV}$) is $10^7$, or nearly four orders of magnitude greater than that for stilbene in micelles, and six orders of magnitude greater than that for dilute stilbene solutions; quenching is nearly (95%) quantitative at $10^{-7}$ M viologen, and is readily detectable at concentrations of less than $10^{-9}$ M. In an unoptimized system, detection levels of as low as $3\times10^{-10}$ M of a protein have been obtained. Under these conditions one molecule of $MV^{2+}$ is effectively quenching at a level of about 1000 repeat units, or approximately one $MV^{2+}$ molecule per polymer chain. Other quenchers of the "molecular" excited state of trans-stilbene are also effective at quenching the fluorescence of MPS-PPV. For example, inorganic ions such as $Cu^{2+}$ ($K_{SV}=10^5$) and $Zn^{2+}$ are effective at quite low concentrations (about $10^{-5}$ to about $10^{-6}$ M) and change the absorption spectra as well.

The remarkably low levels of viologen and other reagents that are effective in quenching the fluorescence for MPS-PPV may be attributed to several phenomena not generally encountered for molecular excited states or even excitonic states of aggregates. To gain an understanding of the mechanism for this dramatic quenching, the system was studied using femtosecond (fs) transient absorption (TA). It is well known that the relatively large energy difference between absorption and emission leads to efficient population inversion and lasing in PPV derivatives. The corresponding stimulated emission (SE) signal provides a dynamic measure of the exciton population. It is also known that aggregation of polymer chains in solution and films leads to quenching of excitons by formation of non-emissive interchain excited states (interchain excitons). The consequences of these processes on the TA dynamics in neat MPS-PPV solutions ($1.5\times10^{-3}$ M) were studied. In the first two picoseconds, the spectrum was found to decay with an apparent blue shift due to the formation of secondary interchain excited-states, and with a competing photoinduced absorption (PA). The temporal evolution of excitons to interchain excited-states could be directly monitored by comparing the dynamics near the peak of the SE (500 nm) and near the zero crossing of the TA spectrum (600 nm, where the exciton cross-section was nearly zero, but the interchain state had a finite PA); the initial decay of the SE (exciton) had a time constant of 1.5 ps, and there was a complementary growth of the interchain excited-states population with the same time constant. Hence, aggregation of MPS-PPV at these relatively high concentrations can provide a direct quenching mechanism in neat MPS-PPV solution. The decay of the SE (500 nm probe) in a $5\times10^{-4}$ M MPS-PPV solution was compared with that for the same solution with addition of $10^{-5}$ $MV^{2+}$. When the MPS-PPV/MV solution was allowed to equilibrate for several minutes, the dynamics showed an increase of 1.5 ps decay component, with no change in the initial 1.5 ps lifetime. This indicated that the dicationic $MV^{2+}$ was promoting additional aggregation of the relatively concentrated MPS-PPV solutions. Interestingly, agitation of the solution (either by gentle shaking or sonication) lead to a dramatic increase in both the magnitude and the rate of SE quenching, with a time constant of 650 fs. The evolution between these two types of dynamics was found fully reversible. This dramatic change in the ultrafast exciton decay points to two competing quenching mechanisms: aggregation quenching due to formation of interchain states, and electron-transfer quenching due to the MPS-PPV/$MV^{2+}$ complex. The addition of divalent cations to anionic polyelectrolytes is known to lead to aggregation, and hence the $MV^{2+}$ intrinsically plays a dual role. The fact that other nonelectron-deficient divalent cations such as $Ca^{2+}$ and $Mg^{2+}$ (which do not quench stilbene) also quench the MPS-PPV emission, but not as efficiently as $MV^{2+}$ ($K_{SV}$ for $Ca^{2+}$ is $10^4$), support this picture of competition between aggregation and electron-transfer quenching. It is also significant that addition of monovalent cations (K+ and $Na^+$) (which do not promote aggregation) had a negligible quenching effect. It is important to note that at MPS-PPV/MV concentrations used in this study, no changes in the quantitative quenching were observed with time, and agitation was not necessary to achieve efficient quenching. Hence, the aggregation quenching likely plays a minor role for MPS-PPV/MV $^{2+}$ at low concentration.

Since the ground state binding of trans-stilbene and even negatively charged assemblies containing trans-stilbene derivatives by $MV^{2+}$ is relatively weak, it was interesting to determine whether the highly effective fluorescence quenching observed in the presence of viologen and other cationic reagents could be reversed. An attractive possibility involves the synthesis and use of a molecule in which a viologen-type quencher and a second recognition unit were combined, separated by a relatively short "tether". Accordingly a biotin-methyl viologen complex (B-MV) was prepared which combined a viologen unit linked to a biotin molecule by a short but flexible tether. B-MV was synthesized by coupling N-(biotinoyl)-N'-(iodoacetyl)ethylenediamine (from Molecular Probes, Inc., Eugene, Oreg.) with 4,4'-bipyridine in N,N'dimethylformamide (DNM) under nitrogen in the dark at room temperature for 24 hours. The final product was purified by silica gel column chromatography. Biotin is an excellent ligand for receptor proteins such as avidin and streptavidin but it was not expected to react with MPS-PPV. Consequently, it was anticipated that, in the absence of receptor protein, the small biotin group in B-MV would not hinder association of the viologen portion of B-MV with MPS-PPV, and that its addition to solution of MPS-PPV would result in strong fluorescence quenching. Since the protein is a much larger molecule than either B-MV or MPS-PPV, and since protein-biotin complexation should be much stronger than that for the polymer-viologen combination, it was anticipated that addition of protein to these "quenched" solutions might reverse the quenching. Indeed, it was found that addition of B-MV to solution of MPS-PPV resulted in fluorescence quenching comparable to that obtained for similar concentrations of $MV^{2+}$ or other electron-deficient cations. Addition of very small amount of avidin reversed this quenching, as anticipated. The amount of avidin necessary to produce significant fluorescence recovery was found to be remarkably low (near $10^{-10}$) and thus demonstrated, even for this non-optimized case, an attractive biosensor.

The system described above was remarkable from a number of different perspectives. The key component is the ionic polymer, which lead to two critical effects. First, amplification of the quenching sensitivity, which was attributed to the large number [>1000] of monomer units per chain, and the high mobility of the exciton along the chain to find the quenching site. Second, once the quenching reagent has been stripped away by the analyte protein, the relatively large sizes of both the MPS-PPV polymer and the protein prevented further association with the quencher, so that the strong fluorescence can be completely recovered. The strategy of using a relatively small amount of a quencher-recognition molecule such as B-MV, and MPS-PPV or a similar polymer as the optical transduction element, results in a sensing device which is effectively in the "off" position (near zero fluorescence background) in the absence of the reagent to be sensed. The very short lifetime of the excited states of quenched polymer (<1 ps) should result in relatively little "photobleaching" in the absence of the molecule to be "sensed" and thus to a potentially robust sensor. The sensitivity and generality of the fluorescence quenching of MPS-PPV (and related polymers) by a wide family of acceptors, and its ready reversal by what is best described as a steric effect when the second recognition element binds to the protein, suggests that the present approach may be applicable to a wide variety of specific sensing applications for proteins and other biological macromolecules.

The sensing applications of MPS-PPV and related polymers are not confined to ionic species or solutions. Neutral, electron deficient aromatics such as 9,10 dicyanoanthracene and nitroaromatics quench in aqueous solution at higher concentrations than for $MV^{2+}$ but still at levels where no "dynamic" quenching could occur given the short (about 1 ns) lifetime of the fluorescent state of MPS-PPV. Even more remarkable quenching is observed for these compounds in solid films of MPS-PPV. Single monolayer films of MPS-PPV were prepared on glass substrates, using polyelectrolyte self-assembly, as described by, e.g., Ghafouri et al., Langmuir, vol. 15, pp. 564 (1999). These films show similar fluorescence and absorption to the solutions of MPS-PPV. Interestingly, exposure of these films to the vapor of nitroaromatics such as nitrobenzene or dinitrotoluene (DNT) lead to substantial quenching of the fluorescence from the films. Rapid quenching was observed from DNT vapor at room temperature. From the vapor pressure of DNT it was determined that the film "senses" (by fluorescence quenching) the nitroaromatic at a level of less than $8 \times 10^{-9}$ M. Since the films of MPS-PPV may be readily overcoated with other films of varying thickness and composition, it should be possible to develop a variety of vapor-based "chemical" sensors of high sensitivity and selectivity.

EXAMPLE 2

Figure 6:
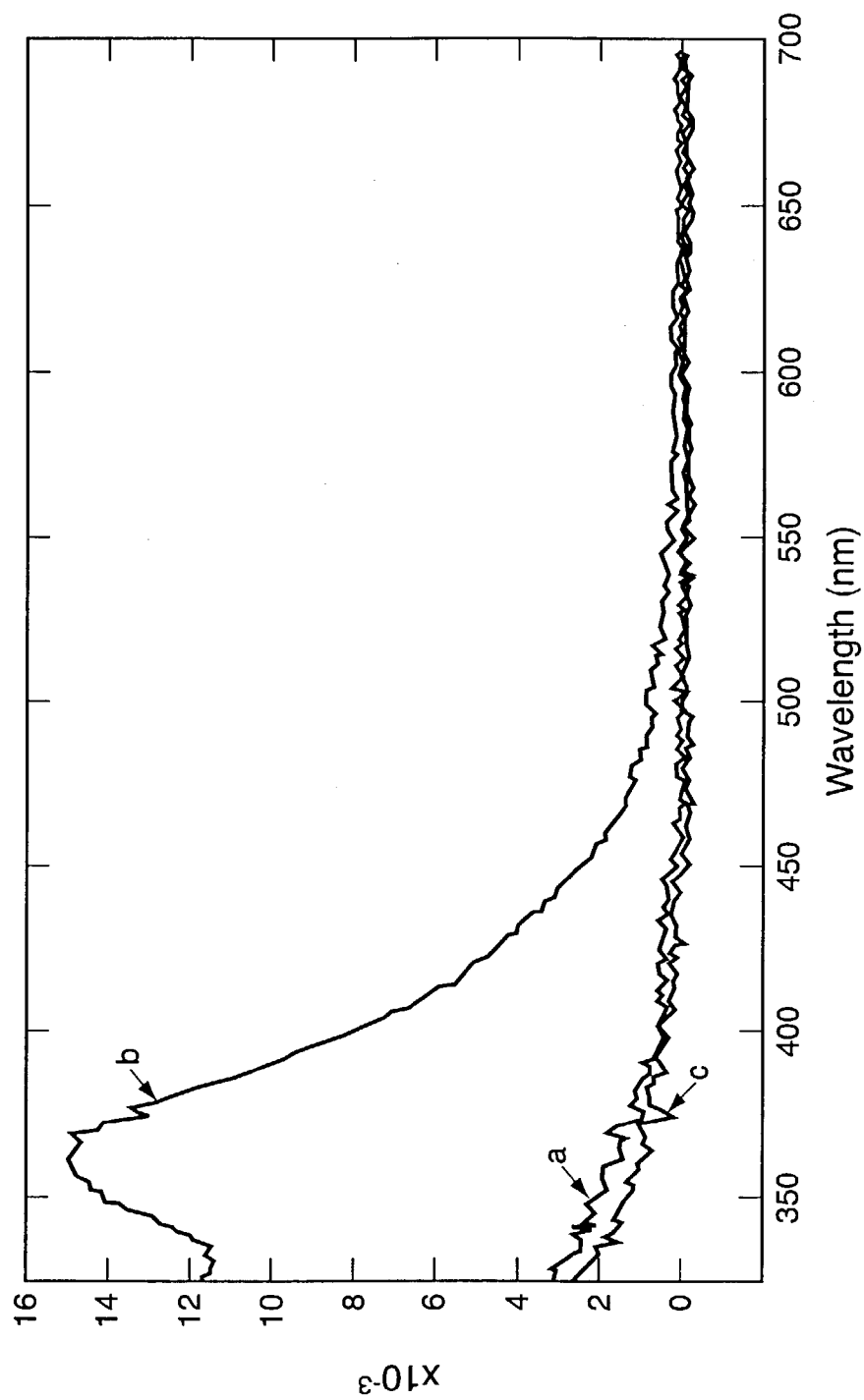
FIG. 6 shows a graph of the ultraviolet-visable (UV-Vis) spectra of (a) MPS-PPV (the polymer), (b) MPS-PPV/MVB (the polymer with the bound intermediate combination) and (c) MPS-PV/MVB in $1\times10^{-5}$M Avidin solution for one minute.
Figure 7:
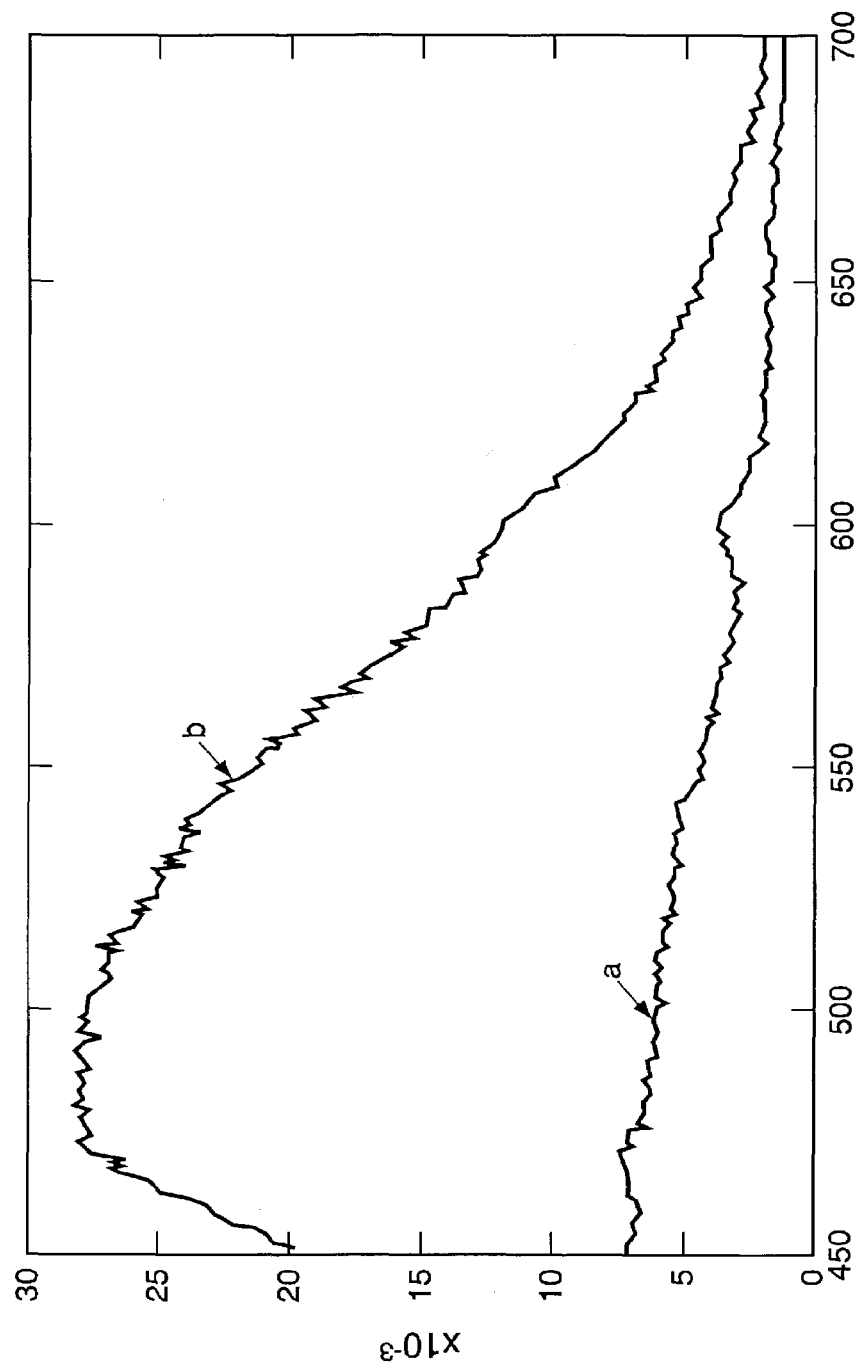
FIG. 7 shows a graph of the photoluminescence (PL) spectra of (a) MPS-PPV/MVB (the polymer with the bound intermediate combination) and (b) MPS-PV/MVB in $1\times10^{-5}$M Avidin solution for one minute.

A glass substrate was prepared by immersion of the glass in an $H_2O_2/H_2SO_4$ (30/70) solution at 70° C. for 1 hour. This substrate was later thoroughly rinsed and sonicated in deionized water for 5 minutes, and this procedure was repeated twice, followed by rinsing with absolute ethanol. This glass substrate was then dried in a 60° C. oven and transferred to a glass jar contained 0.01M of N-[3-(trimethoxysilyl) propyl]ethylenediamine/ethanol solution and soaked overnight. The substrate was removed from the solution and rinsed with absolute ethanol, leaving a monolayer of propyl-ethylenediamine groups chemically bound to the substrate surface. This substrate was later immersed in $10^{-4}$ M MPS-PPV aqueous solution for 5 minutes and then thoroughly rinsed with deionized water. A thin MPS-PPV layer was deposited thereby to the substrate due to electrostatic interactions. The UV-Vis and PL spectra of this sample were then measured. This sample was later immersed in $1\times10^{-3}$ M B-MV solution for 1 minute. UV-Vis and PL spectra were again measured (FIGS. 6 and 7). The PL intensity was completely quenched by the B-MV complex (FIG. 7), and the addition of B-MV was indicated by the altered absorbance spectrum (FIG. 6), which shows a new peak at 367 nm. This completely quenched thin film was later immersed in a $1\times10^{-5}$ M avidin solution for one minute. The PL spectrum of this thin film shows recovery of the PL intensity by a factor of approximately four compared to the quenched state (FIG. 7), and the absorption spectrum shows removal of the B-MV complex by the avidin (disappearance of 367 nm peak, FIG. 6).

From these results, the same turn-on mechanism for a sensor using a thin film containing MPS-PPV/B-MV, and the feasibility of fabricating a solid-state polymer biosensor has been demonstrated.

EXAMPLE 3

Figure 8:
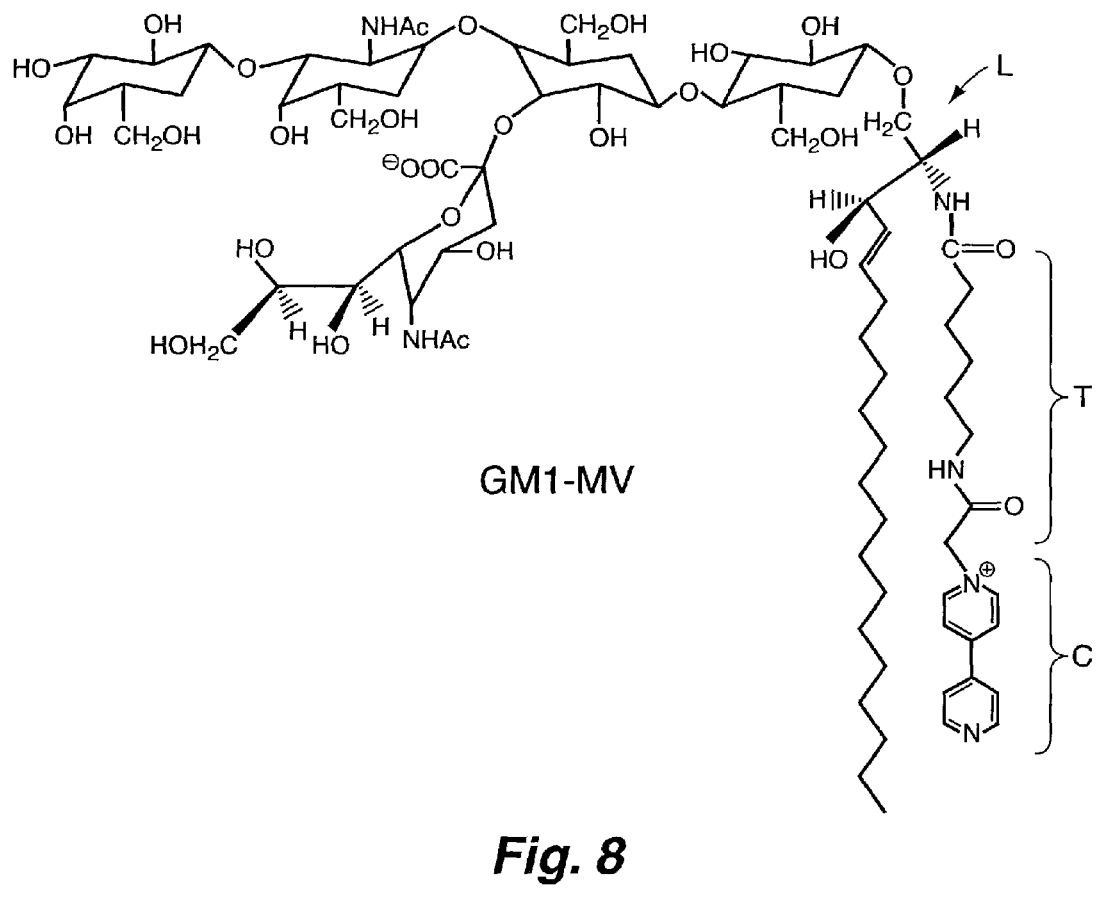

The synthesis of GM1-MV (shown in FIG. 8) was achieved by the reaction of lyso-GM1, which was made based on the literature procedure from GM1(Neurochemicals), with succinimidyl 6-(acetyl-4'-pyridyl-pyridinium) amino)hexanoate in DMF at 60° C. for 12 hours. The product was purified by preparative thin layer chromatography. The starting material, succinimidyl 6-(acetyl-4' -pyridyl-pyridinium)amino)hexanoate was synthesized by coupling succinimidyl 6-(iodoacetyl)amino)hexanoate with 4,4'-bipyridine. In FIG. 8, the methyl viologen portion of the chemical moiety is identified as C; the GM1 portion of the chemical moiety is labeled as L; and the tethering portion of the moiety is labeled T.

EXAMPLE 4

An antibody fragment, $F_V$, synthetically constructed and containing the recognition portion specific for the core protein of hepatitis c was prepared. An aqueous solution of the polymer (phosphate-buffered saline solution) MPS-PPV was treated with a two-fold excess of $Cu^{2+}$ (per repeat unit of polymer) resulting in about a 30% quenching of the polymer fluorescence (observed previously in earlier studies). Upon addition of a small amount of an aqueous PBS solution of the $F_V$ fragment (1 $F_V$ fragment per 23 polymer repeat units and 1 $F_V$ fragment per 46 $Cu^{2+}$) an increase in the quenching to nearly 50% was observed. While not wishing to be bound by the present explanation, the additional quenching has been suggested as due to the formation of a copper (II) complex with a cluster of 1-histidine units "tagged" onto the fragment. Addition of hepatitis c core protein at comparable concentrations to that of the $F_V$ fragment leads to near-complete recovery of the polymer fluorescence. In contrast, addition of hepatitis b core protein (which does not recognize the $F_V$ fragment) to a solution of the copper (II) $F_V$ quenched polymer resulted in no change in the polymer fluorescence.

This example demonstrates the feasibility of sensing using the approach where the ligand is a protein fragment and the bioagent sensed is a protein.

EXAMPLE 5

The DNA-binding domain of Poly(ADP-ribose) polymerase (PARP, EC 2.4.2.30) is expressed in *E. Coli*. This recombinant hexahistidine tagged protein (His-DBD) can recognize and bind to DNA double-strand breaks or nicked DNA in a structure-specific manner. Thus, to a solution of MPS-PV polymer in standard aqueous phosphate buffer saline solution was added $Cu^{2+}$ and then treated with His-DBD. The fluorescence of MPS-PPV is efficiently quenched by the formed Cu-His-DBD complex. Addition of a small amount of a solution of sheared salmon sperm DNA resulted in remarkable increase of the MPS-PPV fluorescence, while in a control experiment, addition of normal salmon sperm DNA solution results negligible change of the MPS-PPV fluorescence.

This example demonstrates the feasibility of sensing DNA using the approach of the present invention.

Although the present invention has been described with reference to specific details, it is not intended that such details should be regarded as limitations upon the scope of the invention, except as and to the extent that they are included in the accompanying claims.

What is claimed is:

1. A separate chemical moiety comprising a recognition element, a tethering element and a property-altering element bound together in combination wherein said recognition element is bound to said tethering element, said tethering element is bound to said property-altering element, and wherein said separate chemical moiety complexes with a polymer having an alterable property selected from the group of luminescence and electrical conductivity.

2. A separate chemical moiety comprising a recognition element, which binds to a target biological agent, and a property-altering element which fluoresces or changes fluorescence to a distinguishable degree bound together by a tethering element, wherein said separate chemical moiety complexes with a fluorescent polymer, wherein, in the presence of binding of said recognition element to said target biological agent, the fluorescence emitted by said polymer is altered from that emitted when said binding between said recognition element and said target biological agent does not occur.

3. The chemical moiety of claim 2, wherein said recognition element is selected from the group consisting of chemical ligands, antibodies, antibody fragments, oligonucleotides, antigens, polypeptides, glycolipids, proteins, enzymes, peptide nucleic acids and polysaccharides.

4. The chemical moiety of claim 2, wherein said property-altering element is selected from the group consisting of methyl viologen, squaraine, metal complexes, fluorescent dyes and electron-accepting moieties.

5. The chemical moiety of claim 2, wherein said tethering element is selected from the group consisting of a single bond, a single divalent atom, a chain of up to 100 carbon atoms in length and a multivalent chemical moiety.

6. The chemical moiety of claim 2, wherein said fluorescent polymer is a luminescent conjugated polymer.

7. The chemical moiety of claim 2, wherein said fluorescent polymer is selected from the group consisting of soluble derivatives of poly(phenylene vinylene), polythiophene, polyphenylene, polydiacetylene, polyacetylene, poly(p-phenylene vinylene), poly(p-naphthalene vinylene) and poly(2,5-pyridyl vinylene).

8. The chemical moiety of claim 2, wherein said fluorescent polymer is a conjugated polyelectrolyte derivative poly(2,5-methoxy propyloxysulfonate phenylene vinylene).

9. The chemical moiety of claim 2, wherein said fluorescent polymer transfers energy to said property-altering element, whereby a change in fluorescence is observed.

10. The chemical moiety of claim 2, wherein said transfer of energy is achieved by electron transfer between said fluorescent polymer and said property-altering element.

11. The chemical moiety of claim 2, wherein said change of fluorescence has a sensitivity as measured by the Stern-Volmer constant Ksv exceeding 1000.

12. The chemical moiety of claim 2, wherein said change of fluorescence has a sensitivity as measured by the Stern-Volmer constant Ksv exceeding 10,000.

13. The chemical moiety of claim 2, wherein said change of fluorescence has a sensitivity as measured by the Stern-Volmer constant Ksv exceeding 100,000.

\* \* \* \* \*